US012053381B2

(12) United States Patent
Cole et al.

(10) Patent No.: US 12,053,381 B2
(45) Date of Patent: Aug. 6, 2024

(54) IMPLANTABLE MEDICAL DEVICE DEPLOYMENT SYSTEM

(71) Applicant: W. L. Gore & Associates, Inc., Newark, DE (US)

(72) Inventors: Daniel S. Cole, Flagstaff, AZ (US); Benjamin A. Smith, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 255 days.

(21) Appl. No.: 17/260,668

(22) PCT Filed: Jul. 17, 2019

(86) PCT No.: PCT/US2019/042248
§ 371 (c)(1),
(2) Date: Jan. 15, 2021

(87) PCT Pub. No.: WO2020/018697
PCT Pub. Date: Jan. 23, 2020

(65) Prior Publication Data
US 2021/0259839 A1 Aug. 26, 2021

Related U.S. Application Data

(60) Provisional application No. 62/699,794, filed on Jul. 18, 2018.

(51) Int. Cl.
*A61F 2/24* (2006.01)
*A61F 2/966* (2013.01)
*A61F 2/95* (2013.01)
(52) U.S. Cl.
CPC .......... *A61F 2/2439* (2013.01); *A61F 2/2418* (2013.01); *A61F 2/2436* (2013.01);
(Continued)

(58) Field of Classification Search
CPC .... A61F 2/2439; A61F 2/2418; A61F 2/2436; A61F 2/9661; A61F 2/9662; A61F 2/966;
(Continued)

(56) References Cited

U.S. PATENT DOCUMENTS 3,953,566 A 4/1976 Gore
4,187,390 A 2/1980 Gore
(Continued)

FOREIGN PATENT DOCUMENTS

CN 104414692 A 3/2015
EP 2637576 A1 9/2013
(Continued)

OTHER PUBLICATIONS

Eigler et al., "Cardiac Unloading with an Implantable Interatrial Shunt in Heart Failure: Serial Observations in an Ovine Model of Ischemic Cardiomyopathy", Structural Heart, vol. 1, No. (1-2), 2017, 'pp. 40-48.
(Continued)

*Primary Examiner* — Kelly J Bekker
*Assistant Examiner* — Andrew P. Restaino

(57) ABSTRACT

Various aspects of the present disclosure are directed toward apparatuses, systems (200), and methods for deploying a medical device (202). In certain instances, the medical device (202) may be a shunt device. In addition, the apparatuses, systems (200), and methods may include one or more constraining lines (212) arranged through a portion of the implantable medical device (202) and one or more release lines (216) configured to engage the one or more constraining lines (212).

22 Claims, 9 Drawing Sheets

(52) U.S. Cl.
CPC ......... *A61F 2/9661* (2020.05); *A61F 2/9662* (2020.05); *A61F 2002/9511* (2013.01); *A61F 2/966* (2013.01); *A61F 2220/0083* (2013.01)

(58) Field of Classification Search
CPC ..... A61F 2002/9511; A61F 2220/0083; A61B 2017/1139; A61B 17/11; A61B 2017/00623; A61B 2017/00243
See application file for complete search history.

(56) References Cited

U.S. PATENT DOCUMENTS

| | | | |
|---|---|---|---|
| 5,276,276 | A | 1/1994 | Gunn |
| 5,334,217 | A | 8/1994 | Das |
| 5,683,411 | A | 11/1997 | Kavteladze et al. |
| 5,824,055 | A | 10/1998 | Spiridigliozzi et al. |
| 5,944,738 | A | 8/1999 | Amplatz et al. |
| 6,042,602 | A | 3/2000 | Wells |
| 6,042,605 | A | 3/2000 | Martin et al. |
| 6,077,291 | A | 6/2000 | Das |
| 6,080,182 | A | 6/2000 | Shaw et al. |
| 6,461,665 | B1 | 10/2002 | Scholander |
| 6,616,675 | B1 | 9/2003 | Evard et al. |
| 6,911,037 | B2 | 6/2005 | Gainor et al. |
| 6,926,670 | B2 | 8/2005 | Rich et al. |
| 7,001,409 | B2 | 2/2006 | Amplatz |
| 7,049,380 | B1 | 5/2006 | Chang et al. |
| 7,236,821 | B2 | 6/2007 | Cates et al. |
| 7,462,675 | B2 | 12/2008 | Chang et al. |
| 7,871,659 | B2 | 1/2011 | Cook et al. |
| 7,887,562 | B2 | 2/2011 | Young et al. |
| 7,901,702 | B2 | 3/2011 | Schwarz |
| 8,021,331 | B2 | 9/2011 | Herweck et al. |
| 8,043,360 | B2 | 10/2011 | McNamara et al. |
| 8,048,440 | B2 | 11/2011 | Chang et al. |
| 8,091,556 | B2 | 1/2012 | Keren et al. |
| 8,480,707 | B2 | 7/2013 | Pavcnik et al. |
| 8,545,525 | B2 | 10/2013 | Surti et al. |
| 8,696,693 | B2 | 4/2014 | Najafi et al. |
| 8,715,300 | B2 | 5/2014 | Najafi et al. |
| 8,728,103 | B2 | 5/2014 | Surti et al. |
| 9,241,695 | B2 | 1/2016 | Peavey et al. |
| 9,314,556 | B2 | 4/2016 | Tuseth |
| 9,358,371 | B2 | 6/2016 | McNamara et al. |
| 9,399,085 | B2 | 7/2016 | Cleek et al. |
| 9,456,812 | B2 | 10/2016 | Finch et al. |
| 9,545,300 | B2 | 1/2017 | Cully et al. |
| 9,554,786 | B2 | 1/2017 | Carley et al. |
| 9,629,715 | B2 | 4/2017 | Nitzan et al. |
| 9,636,094 | B2 | 5/2017 | Aurilia et al. |
| 9,649,481 | B2 | 5/2017 | Sadanand |
| 9,681,948 | B2 | 6/2017 | Levi et al. |
| 9,757,107 | B2 | 9/2017 | McNamara et al. |
| 9,775,591 | B2 | 10/2017 | Delgado et al. |
| 9,861,346 | B2 | 1/2018 | Callaghan |
| 9,878,162 | B2 | 1/2018 | Mika et al. |
| 9,949,728 | B2 | 4/2018 | Cahill |
| 10,806,458 | B2 * | 10/2020 | Todd .......... A61F 2/90 |
| 2002/0169475 | A1 * | 11/2002 | Gainor .......... A61B 17/0057 606/213 |
| 2002/0173742 | A1 | 11/2002 | Keren et al. |
| 2003/0139819 | A1 | 7/2003 | Beer et al. |
| 2004/0063805 | A1 | 4/2004 | Pacetti et al. |
| 2004/0073242 | A1 | 4/2004 | Chanduszko |
| 2005/0049675 | A1 | 3/2005 | Wallace |
| 2006/0009800 | A1 | 1/2006 | Christianson et al. |
| 2006/0100687 | A1 * | 5/2006 | Fahey .......... A61M 25/0051 606/191 |
| 2006/0198866 | A1 | 9/2006 | Chang et al. |
| 2007/0244518 | A1 | 10/2007 | Callaghan |
| 2007/0282430 | A1 | 12/2007 | Thommen et al. |
| 2008/0249562 | A1 | 10/2008 | Cahill |
| 2008/0262518 | A1 | 10/2008 | Freudenthal |
| 2009/0024042 | A1 | 1/2009 | Nunez et al. |
| 2009/0099640 | A1 * | 4/2009 | Weng .......... A61F 2/95 623/1.11 |
| 2009/0221923 | A1 | 9/2009 | Uemura et al. |
| 2010/0049313 | A1 | 2/2010 | Alon et al. |
| 2010/0094401 | A1 | 4/2010 | Kolbel et al. |
| 2011/0071623 | A1 | 3/2011 | Finch et al. |
| 2011/0071624 | A1 | 3/2011 | Finch et al. |
| 2011/0098767 | A1 | 4/2011 | Sugimachi et al. |
| 2011/0153010 | A1 | 6/2011 | Hanna |
| 2011/0184439 | A1 | 7/2011 | Anderson et al. |
| 2011/0257723 | A1 | 10/2011 | McNamara |
| 2011/0295183 | A1 | 12/2011 | Finch et al. |
| 2011/0295366 | A1 | 12/2011 | Finch et al. |
| 2012/0136385 | A1 | 5/2012 | Cully |
| 2013/0165967 | A1 | 6/2013 | Amin et al. |
| 2013/0178784 | A1 | 7/2013 | McNamara et al. |
| 2013/0281988 | A1 | 10/2013 | Magnin et al. |
| 2014/0012368 | A1 | 1/2014 | Sugimoto et al. |
| 2014/0018911 | A1 * | 1/2014 | Zhou .......... A61F 2/2436 623/2.11 |
| 2014/0128795 | A1 | 5/2014 | Keren et al. |
| 2014/0142617 | A1 | 5/2014 | Larsen et al. |
| 2014/0207153 | A1 | 7/2014 | Najafi et al. |
| 2014/0214149 | A1 | 7/2014 | Kuraguntla et al. |
| 2014/0222040 | A1 | 8/2014 | Park et al. |
| 2014/0343670 | A1 | 11/2014 | Bakis et al. |
| 2015/0039084 | A1 | 2/2015 | Levi et al. |
| 2015/0142049 | A1 | 5/2015 | Delgado et al. |
| 2015/0313596 | A1 | 11/2015 | Todd |
| 2015/0313599 | A1 | 11/2015 | Johnson et al. |
| 2016/0058452 | A1 | 3/2016 | Brenneman et al. |
| 2016/0331566 | A1 | 11/2016 | Kheradvar et al. |
| 2017/0028194 | A1 | 2/2017 | Bonner et al. |
| 2017/0042705 | A1 | 2/2017 | Cook et al. |
| 2017/0105711 | A1 | 4/2017 | Masters |
| 2017/0106176 | A1 | 4/2017 | Taft et al. |
| 2017/0172766 | A1 | 6/2017 | Vong et al. |
| 2017/0196673 | A1 | 7/2017 | Cully et al. |
| 2017/0224323 | A1 | 8/2017 | Rowe et al. |
| 2017/0281339 | A1 | 10/2017 | Levi et al. |
| 2017/0319823 | A1 | 11/2017 | Yacoby et al. |
| 2018/0000580 | A1 | 1/2018 | Wallace et al. |
| 2018/0055629 | A1 | 3/2018 | Oba et al. |
| 2018/0098772 | A1 | 4/2018 | Goldshtein et al. |
| 2018/0280667 | A1 | 10/2018 | Keren |
| 2019/0282178 | A1 | 9/2019 | Volosin et al. |
| 2020/0038567 | A1 | 2/2020 | Siess et al. |
| 2020/0179663 | A1 | 6/2020 | McDaniel et al. |
| 2020/0196876 | A1 | 6/2020 | Minor et al. |
| 2020/0196943 | A1 | 6/2020 | Minor et al. |
| 2020/0196944 | A1 | 6/2020 | Minor et al. |
| 2020/0197178 | A1 | 6/2020 | Vecchio |
| 2021/0290214 | A1 | 9/2021 | Cole et al. |
| 2023/0074508 | A1 | 3/2023 | Cole et al. |
| 2023/0116796 | A1 | 4/2023 | Cole et al. |

FOREIGN PATENT DOCUMENTS

| | | |
|---|---|---|
| GB | 1355373 A | 6/1974 |
| GB | 1506432 A | 4/1978 |
| GB | 1509023 A | 4/1978 |
| JP | 07-502918 A | 3/1995 |
| JP | 2001-519694 A | 10/2001 |
| JP | 2002-248105 A | 9/2002 |
| JP | 2005-528181 A | 9/2005 |
| JP | 2008-512139 A | 4/2008 |
| JP | 2008-512211 A | 4/2008 |
| JP | 2010-505481 A | 2/2010 |
| JP | 2012-500665 A | 1/2012 |
| JP | 2013-517890 A | 5/2013 |
| JP | 2014-503246 A | 2/2014 |
| JP | 2016-511656 A | 4/2016 |
| JP | 2016-518948 A | 6/2016 |
| JP | 2017-513545 A | 6/2017 |
| JP | 2017-515631 A | 6/2017 |
| JP | 2021-531097 A | 11/2021 |
| WO | 93/13712 A1 | 7/1993 |
| WO | 98/42276 A1 | 10/1998 |
| WO | 2003/103476 A2 | 12/2003 |

(56) References Cited

FOREIGN PATENT DOCUMENTS

| WO | 2004/091411 A2 | 10/2004 |
| WO | 2008/040555 A2 | 4/2008 |
| WO | 2009/137755 A2 | 11/2009 |
| WO | 2010/022138 A2 | 2/2010 |
| WO | 2011/093941 A2 | 8/2011 |
| WO | 2012/091809 A1 | 7/2012 |
| WO | 2014/018977 A1 | 1/2014 |
| WO | 2014/150106 A1 | 9/2014 |
| WO | 2015/109027 A2 | 7/2015 |
| WO | 2017/118738 A1 | 7/2017 |
| WO | 2020/018697 A1 | 1/2020 |

OTHER PUBLICATIONS

Feldman et al., "Transcatheter Interatrial Shunt Device for the Treatment of Heart Failure Rationale and Design of the Randomized Trial to REDUCE Elevated Left Atrial Pressure in Heart Failure (REDUCE LAP-HF I)", Circulation Heart failure, vol. 9, No. 7, 2016, pp. 1-10.

Gregg et al., "Interatrial Shunting for Heart Failure The V-WAVE SHUNT", Presentation at the Transcatheter Cardiovascular Therapeutics (TCT) Congress in Denver, Colorado, 2017, 18 pages.

International Preliminary Report on Patentability received for PCT Patent Application No. PCT/US2019/065610, mailed on Jun. 24, 2021, 9 pages.

International Search Report and Written Opinion received for PCT Patent Application No. PCT/US2019/065610, mailed on Mar. 26, 2020, 12 pages.

International Search Report and Written Opinion received for PCT Patent Application No. PCT/US2021/013421, mailed on Apr. 28, 2021, 20 pages.

Søndergaard et al., "Transcatheter treatment of heart failure with preserved or mildly reduced ejection fraction using a novel interatrial implant to lower left atrial pressure", European Journal of Heart Failure, vol. 16, 2014, pp. 796-801.

International Search Report and Written Opinion received for PCT Patent Application No. PCT/US2019/042248, mailed on Oct. 23, 2019, 18 pages.

Wei, X., Liu, X., Rosenzweig, A. What do we know about the cardiac benefits of exercise? Trends in Cardiovascular Medicine; 25(6): 537-539. Aug. 2015 (Year: 2015).

International Preliminary Report on Patentability received for PCT Patent Application No. PCT/US2021/013411, mailed on Jul. 28, 2022, 9 pages.

International Preliminary Report on Patentability received for PCT Patent Application No. PCT/US2021/013421, mailed on Jul. 28, 2022, 12 pages.

\* cited by examiner

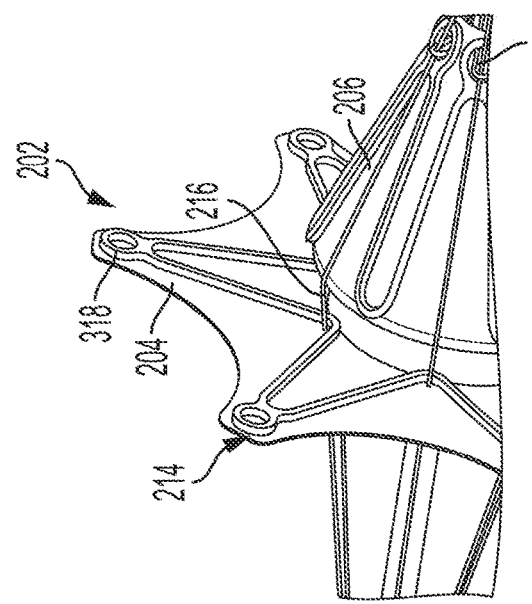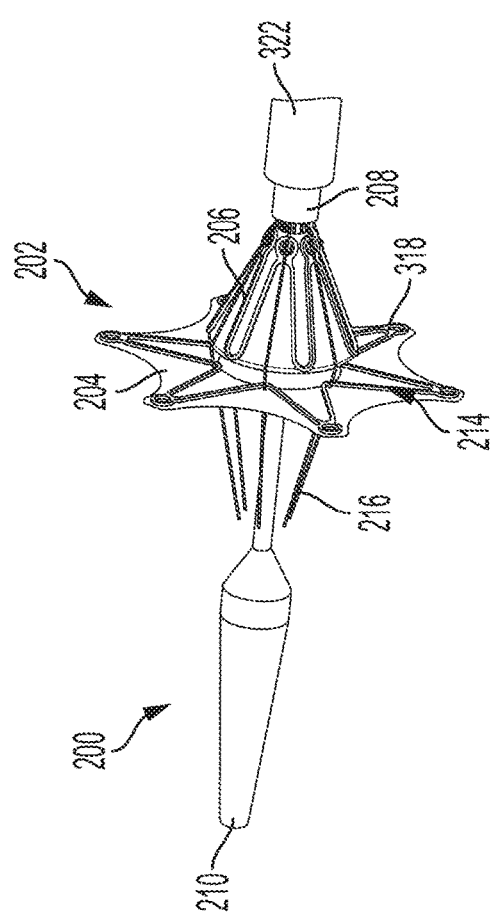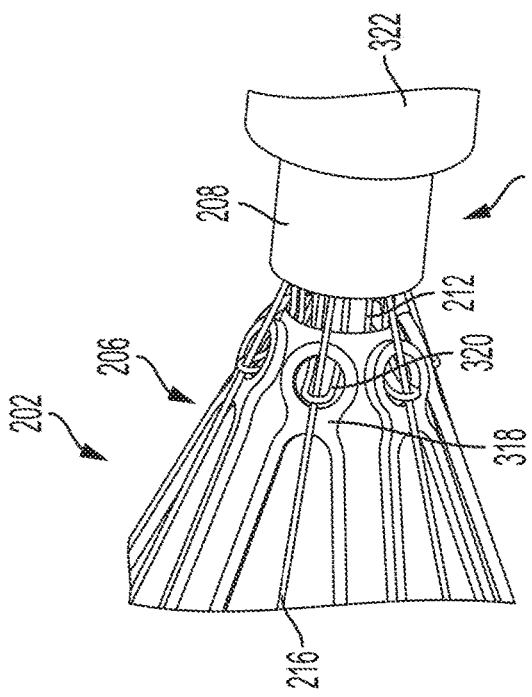

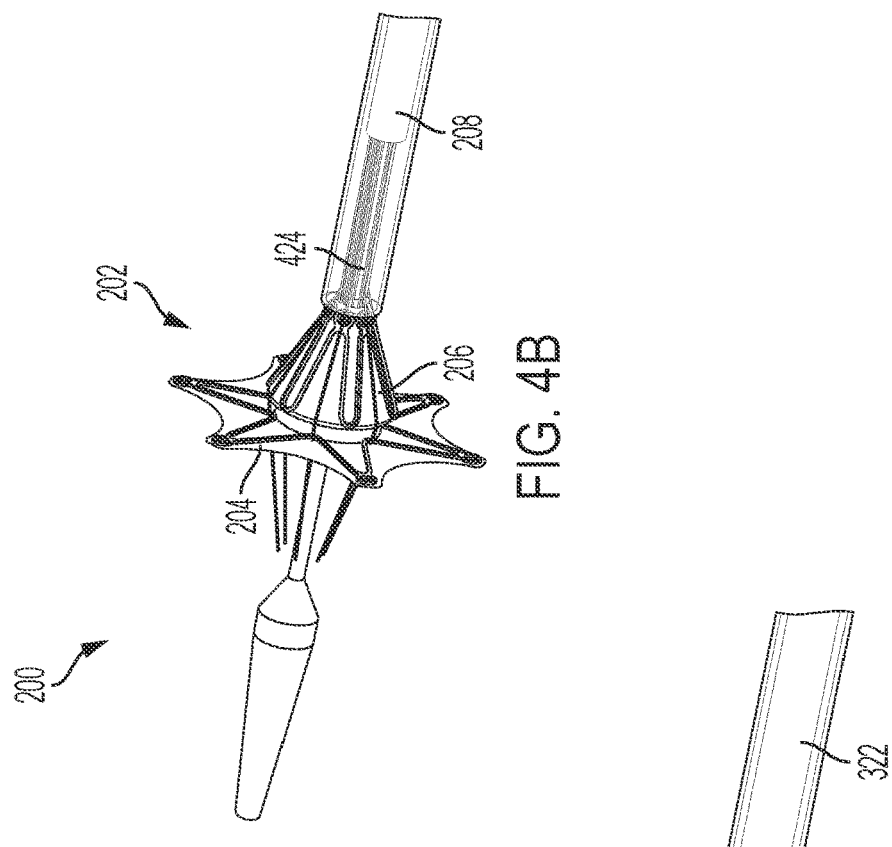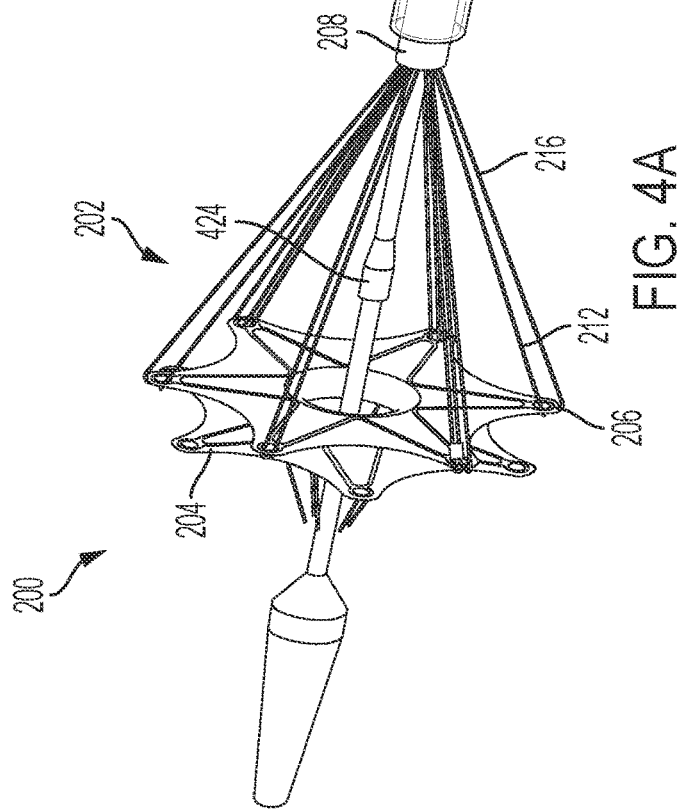

IMPLANTABLE MEDICAL DEVICE DEPLOYMENT SYSTEM

PRIORITY CLAIM

This application is a national phase application of PCT Application No. PCT/US2019/042248, internationally filed on Jul. 17, 2019, which claims the benefit of Provisional Application No. 62/699,794, filed Jul. 18, 2018, which is are incorporated herein by reference in its their entireties for all purposes.

FIELD

The present disclosure relates generally to implantable medical device delivery, and more specifically to methods, systems, and apparatuses for delivery of implantable medical devices such as shunts and heart valves.

BACKGROUND

Previously deployment methods for implantable medical devices such as interatrial shunt devices have difficulty properly positioning the devices. In addition, many of these systems do not have the ability to recapture or reposition a deployed device in instances where the deployment is not desirable. Therefore, a need exists for device delivery systems robust enough to deliver, reposition, recapture if needed and release the device when properly deployed.

SUMMARY

In one example ("Example 1"), a deployment system for an implantable medical device includes: a catheter; one or more constraining lines arranged through one or more eyelets of the implantable medical device, the one or more constraining lines being configured to collapse portions of the implantable medical device toward the catheter; and one or more release lines configured to engage the one or more constraining lines and maintain contact between the implantable medical device and the one or more constraining lines during deployment.

In another example ("Example 2"), further to the system of Example 1, the one or more constraining lines are configured to engage eyelets on at least a first side of the implantable medical device.

In another example ("Example 3"), further to the system of any one of Examples 1-2, the system also includes a sheath arranged about the catheter and configured to capture the collapsed implantable medical device.

In another example ("Example 4"), further to the system of Example 3, the sheath is configured to constrain the implantable medical device.

In another example ("Example 5"), further to the system of any one of Examples 1-4, the one or more release lines are configured to withdraw to release the one or more constraining lines.

In another example ("Example 6"), further to the system of Example 5, the one or more constraining lines include a constraining loop at a distal end of the one or more constraining lines, and the one or more release lines are arranged through the constraining loop of the one or more constraining lines maintain contact between the implantable medical device and the one or more constraining lines during deployment.

In another example ("Example 7"), further to the system of any one of Examples 1-6, the one or more constraining lines are one or more constraining wires.

In another example ("Example 8"), further to the system of any one of Examples 1-7, the system also includes a stop arranged on the catheter configured to limit movement of the implantable medical device in a direction opposite that of a direction tension is applied to the one or more constraining lines.

In another example ("Example 9"), further to the system of any one of Examples 1-7, the system also includes one or more stops arranged distal to a distal end of the one or more constraining lines and configured to prevent the distal end of the one or more constraining lines from withdrawing from the one or more eyelets of the implantable medical device prior to removal of the one or more release lines.

In another example ("Example 10"), further to the system of any one of Examples 1-9, the one or more release lines are configured to facilitate deployment and act as a ramp to guide the implantable medical device from a sheath.

In another example ("Example 11"), further to the system of any one of Examples 1-10, the implantable medical device is one of a shunt device, a heart valve, or a valved conduit.

In one example ("Example 12"), a deployment system includes an implantable medical device; a sheath arranged configured to hold the implantable medical device in a collapsed configuration; one or more constraining lines arranged through a portion of the implantable medical device and configured to collapse portions of the implantable medical device toward the catheter in response to tension applied to the one or more constraining lines and allow expansion of the implantable medical device in response to release of the tension; and one or more release lines configured to engage the one or more constraining lines and maintain contact between the implantable medical device and the one or more constraining lines during deployment and withdraw to release the one or more constraining lines to deploy the implantable medical device to a deployed configuration.

In another example ("Example 13"), further to the system of Example 12, the implantable medical device includes eyelets arranged about a circumference of the implantable medical device and the one or more constraining lines are arranged through the eyelets.

In another example ("Example 14"), further to the system of Example 12, each of the one or more constraining lines include a constraining loop at a distal end of the one or more constraining lines, and the one or more release lines are arranged through the constraining loop of the one or more constraining lines maintain contact between the implantable medical device and the one or more constraining lines during deployment.

In another example ("Example 15"), further to the system of Example 12, at least one of the one or more constraining lines and the one or more release lines are coupled to the catheter near a distal end thereof.

In another example ("Example 16"), further to the system of Example 15, the catheter includes a tip coupled to the distal end of the catheter, and at least one of the one or more constraining lines and the one or more release lines are coupled to the catheter adjacent the tip.

In another example ("Example 17"), a method of deploying an implantable medical device includes arranging a catheter at a target location with the implantable medical device arranged within a collapsed configuration within a sheath; allowing expansion of at least a portion of the implantable medical device by releasing tension on one or more constraining lines arranged through one or more eyelets of the implantable medical device; and releasing the one or more constraining lines from the implantable medical device by removing one or more release lines engage with the one or more constraining lines.

In another example ("Example 18"), further to the method of Example 17, the method also includes comprising advancing the sheath to deploy a first side of the implantable medical device and wherein allowing expansion of the portion of the implantable medical device includes allowing expansion of a second side of the implantable medical device by releasing tension on the one or more constraining lines.

In another example ("Example 19"), further to the method of Example 18, the method also includes reconstraining the implantable medical device by applying tension to the one or more constraining lines and retracting the implantable medical device within the delivery sheath.

In another example ("Example 20"), further to the method of Example 18, the method also includes deploying the second side of the implantable medical device by releasing tension applied to the constraining lines.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 3A is an example delivery system and shunt device in accordance with an embodiment.

FIG. 3B is first close-up view of the delivery system and shunt device, shown in FIG. 3A, in accordance with an embodiment.

FIG. 3C is second close-up view of the delivery system and shunt device, shown in FIGS. 3A-3B, in accordance with an embodiment.

FIG. 4A is an example delivery system including a stop and shunt device in a first configuration in accordance with an embodiment.

FIG. 4B is the delivery system and shunt device, shown in FIG. 4A, in a second configuration in accordance with an embodiment.

DETAILED DESCRIPTION

Definitions and Terminology

Figure 1:
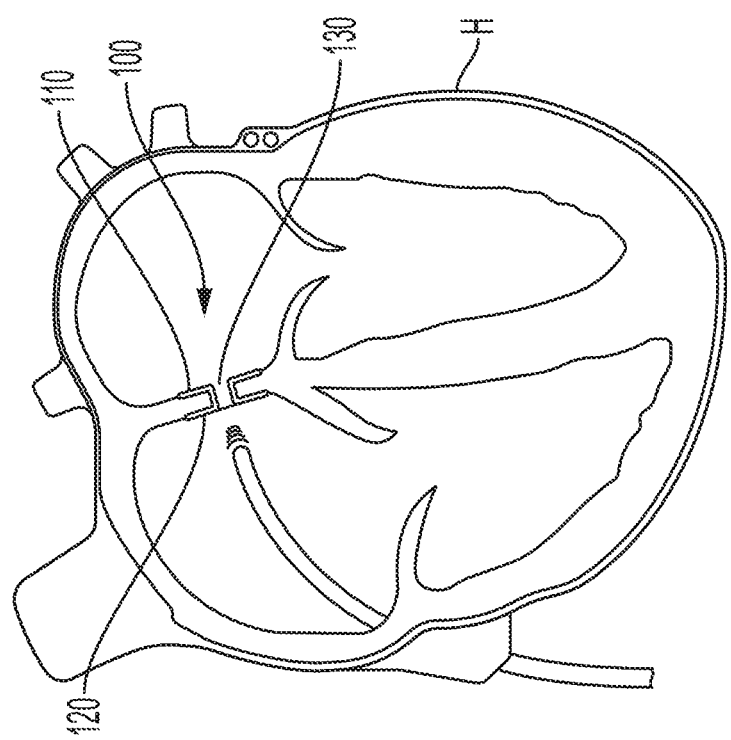
FIG. 1 is an example implantable medical device in accordance with an embodiment.

This disclosure is not meant to be read in a restrictive manner. For example, the terminology used in the application should be read broadly in the context of the meaning those in the field would attribute such terminology.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, minor adjustments made to optimize performance and/or structural parameters in view of differences in measurements associated with other components, particular implementation scenarios, imprecise adjustment and/or manipulation of objects by a person or machine, and/or the like, for example. In the event it is determined that individuals having ordinary skill in the relevant arts would not readily ascertain values for such reasonably small differences, the terms "about" and "approximately" can be understood to mean plus or minus 10% of the stated value.

Description of Various Embodiments

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

FIG. 1 illustrates an example implantable medical device 100 in accordance with an embodiment. The implantable medical device 100 is shown implanted within a heart H of a patient. The device 100 is shown arranged between the patient's left atrium LA and right atrium RA. In some instances, the device 100 may be used within the heart H, for example, between the left and right atriums LA, RA. As shown, the device 100 generally includes a first frame component 110 arranged on a first side of a septum (e.g., within the right atrium RA), a second frame component 120 arranged on a second side of the septum (e.g., within the left atrium LA), and a conduit 130 extending through the septum. A needle may be used to create an opening in the septum. The implantable medical device 100 may be a shunt device with the conduit 130 being a fluid flow lumen between the sides of the implantable medical device 100.

Figure 2:
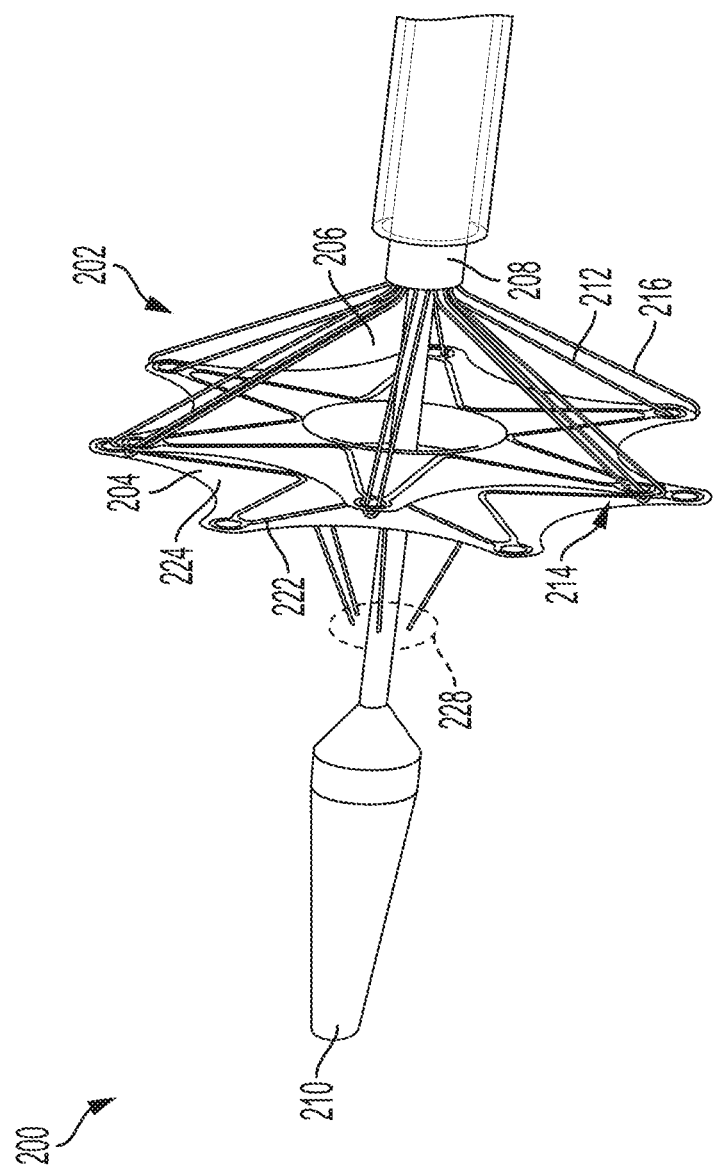
FIG. 2 is an example delivery system and shunt device in accordance with an embodiment.

FIG. 2 is an example delivery system 200 and implantable medical device 202 such as a shunt device in accordance with an embodiment. The implantable medical device 202 may include a first side 204 and a second side 206. Each of the sides 204, 206 may include a stent element 222 and a membrane component 224 as shown in FIG. 2. The sides 204, 206 are configured to conform to the patient's anatomy (i.e., the first side of the septum, for example). The first side 204 and the second side 206 may be separate and distinct components with a flexible interconnection that connects the two sides in a manner that decouples forces acting on the first side 204 from forces acting on the second side 206. For example, the first side 204 and the second side 206 may be free to move, in response to movement of the patient's anatomy, separately from one another. In this manner, forces acting on one of the first side 204 and the second side 206 are maintained within the other of the first side 204 and the second side 206. The forces acting on one of the first side 204 and the second side 206 may be isolated to the frame component to which the force is acted on.

The delivery system 200 includes a catheter 208 configured to delivery through a patient's vascular to a delivery site. In certain instances, the delivery system 200 includes a tip 210, that may be atraumatic and may be radiopaque, arranged at a distal end of the catheter 208. The delivery system 200 may also include one or more constraining lines 212 arranged through a portion of the implantable medical device 202. The one or more constraining lines 212 are configured to collapse portions of the implantable medical device 202 toward the catheter 208. In certain instances, the implantable medical device 202 includes a series of lobes or radially extending loops 214. The lobes or radially extending loops 214 are formed by portions of the stent element 222 and the membrane component 224 and may be on each of the first side 204 and the second side 206. In certain instances, the one or more constraining lines 212 are configured to collapse the lobes or radially extending loops 214 of one or both of the sides 204, 206 toward the catheter 208.

The delivery system 200 may also include one or more release lines 216 are configured to engage the one or more constraining lines 212 and maintain contact between the implantable medical device 202 and the one or more constraining lines 212 during deployment. In certain instances, the release lines 216 may embed or nest within the tip 210. In other instances, a skirt 228 may be positioned proximal to the tip 210. The release lines 216 may be tucked into the skirt 228.

Examples of materials for the constraining lines 212 or release lines 216 may be metals such as stainless steels, cobalt-chromium alloys and nitinol. The release lines can also be formed from high strength polymer fibers such as ultra-high molecular weight polyethylene fibers or aramid fibers. However, any material capable of providing sufficient tension is within the scope of the present disclosure. The constraining lines 212 or release lines 216 may also be formed from a film such as kapton, a polymer (e.g., Polyether ether ketone (Peek)), laser cut of a hypotube, or a cut polymer tube).

FIG. 3A illustrates features of delivery system 200 and implantable medical device 202 employed in accordance with an embodiment. As shown in FIG. 3A, the implantable medical device 202 is in a partially collapsed or constrained configuration with the second side 206 (e.g., a proximal side) being collapsed or constrained. In addition, the first side 204 and the second side 206 may include eyelets 318.

In certain instances, the eyelets 318 may be arranged on end portions of the lobes or radially extending loops 214. In certain instances, each of the lobes or radially extending loops 214 include an eyelet 318, and in other instances, selected ones or pairs of the lobes or radially extending loops 214 include eyelets 318. In addition, the lobes or radially extending loops 214 of the second side 206 may include eyelets 318 with the lobes or radially extending loops 214 of the first side 204 not including eyelets. In other instances, the lobes or radially extending loops 214 of the first side 204 may include eyelets 318 with the lobes or radially extending loops 214 of the second side 206 not including eyelets. Further and as shown, the lobes or radially extending loops 214 of both sides 204, 206 include the eyelets 318.

In certain instances and as shown in further detail in FIGS. 3B-C, the one or more constraining lines 212 are configured to engage the eyelets 318. The constraining lines 212 may be arranged through the eyelets 318. In addition, the constraining lines 212 may engage (and be arrange through) only the eyelets 318 on the second (proximal) side 206 of the implantable medical device 202. In other instances, the constraining lines 212 may engage (and be arrange through) only the eyelets 318 on the first (distal) side 204 of the implantable medical device 202. Further, the constraining lines 212 may engage (and be arrange through) the eyelets 318 on both the first (distal) side 204 and the second (proximal) side 206 of the implantable medical device 202. In instances where the implantable medical device 202 does not include eyelets 318, the constraining lines 212 and release lines 216 may be arranged through membrane component 224.

To release or deploy the implantable medical device 202, the one or more release lines 216 are withdrawn to release the one or more constraining lines 212. In certain instances and as shown in particular with reference to FIG. 3, the one or more constraining lines 212 include a constraining loop 320 at a distal end of the one or more constraining lines 212. The one or more release lines 216 may be arranged through the constraining loop 320 of the one or more constraining lines 212 and maintain contact between the implantable medical device 202 and the one or more constraining lines 212 during deployment. The one or more release lines 216 are withdrawn through the constraining loop 320 to release the one or more constraining lines 212. In certain instances, the implantable medical device 202 includes only membrane material between the first side 202 and the second side 204. As shown, the release lines 216 are configured to facilitate deployment and act as a ramp to guide the implantable medical device 202 from a sheath. The release lines 216 are configured to pull down the first side 204 of the implantable medical device 202 radially.

Tension applied to the constraining lines 212 to collapse portions of the implantable medical device 202 toward the catheter 208. More specifically, the lobes or radially extending loops 214 (radially projecting) of one or both sides 204, 206 are collapsed. Tension on an end of the constraining lines 212 not arranged with the implantable medical device 202 retracts the constraining lines 212 into the catheter 208. In certain instances, the sheath 322 may also be used to facilitate delivery and constrain the implantable medical device 202. After the lobes or radially extending loops 214 of one or both sides 204, 206 are collapsed, the sheath 322 may be advanced to further constrain the lobes or radially extending loops 214 of one or both sides 204, 206. In certain instances, the lobes or radially extending loops 214 of the second side 206 are collapsed, and the sheath 322 is advanced to constrain the lobes or radially extending loops 214 of the first side 204. The sheath 322 may be advanced to the tip 210. As the he constraining lines 212 are retracted into the catheter 208, the implantable medical device 202 may be collapsed within the sheath 322.

In one example of a deployment sequence, to deploy the implantable medical device 202, the above note constraining sequence is reversed. Once the tip 210 and catheter 208 is across the septum the sheath 322 is retracted and the lobes or radially extending loops 214 of the first side 204 are deployed. The sheath 322 may be pulled back so that the lobes or radially extending loops 214 of the first side 204 apply tension to the septum. Prior to release of the constraining lines 212 and the release lines 216, the positioning of the implantable medical device 202 can be evaluated. If the positioning is not satisfactory or desirable, the implantable medical device 202 may be reconstrained and repositioned. To reconstrain and reposition the implantable medical device 202, the constraining sequence described above may be followed (e.g., tension may be applied to the one or more constraining lines 212 and the implantable medical device 202 may be retracted within the sheath 322). The second side 206 of the implantable medical device 202 may be deployed by releasing tension applied to the constraining lines 212.

After the implantable medical device 202 is positioned, the constraining lines 212 and the release lines 216 are released so that the lobes or radially extending loops 214 of the second side 206 are deployed. The release lines 216 are then retracted back to release the constraining loop 320 of the one or more constraining lines 212 from the eyelets 318. The one or more constraining lines 212 and the release lines 216 are coupled to separate pull mechanisms to apply tension to the constraining lines 212 and the release lines 216. This may facilitate simultaneous manipulation of the constraining lines 212 and simultaneous manipulation of the release lines 216. The constraining lines 212 and the release lines 216 can be released simultaneously or individually depending on the deployment to maintain stability of the implantable medical device 202 during deployment.

In certain instances, the constraining lines 212 are constraining wires (e.g., formed of a metal or metal-type material). In this manner, the constraining lines 212 may have sufficient strength and flexibility to constrain the implantable medical device 202. Using the system 200 as described herein may be beneficial, as compared to a more rigid system, as the deployment system 200 is configured to allow the catheter 208 to be at a smaller acute angle to the septum.

FIG. 4A is a delivery system 200 including an optional stop 424 and implantable medical device 202 in a first configuration in accordance with an embodiment. During deployment and pull back of the sheath 322, the stop 424 pushes the device out of the sheath 322 as the sheath is retracted.

In certain instances, the constraining lines 212 may be fixed to catheter 208. To constrain the implantable medical device 202, in these instances, the catheter 208 is pulled back relative to the outer sheath 322. The sheath 322 pulls the lobes or radially extending loops 214 of one or both sides 204, 206 onto itself as shown in FIG. 4B. The stop 424 is configured to limit movement of the implantable medical device 202 in a direction opposite that of a direction tension is applied to the one or more constraining lines 202 or in a direction opposite that of the sheath 322 movement.

Figure 5:
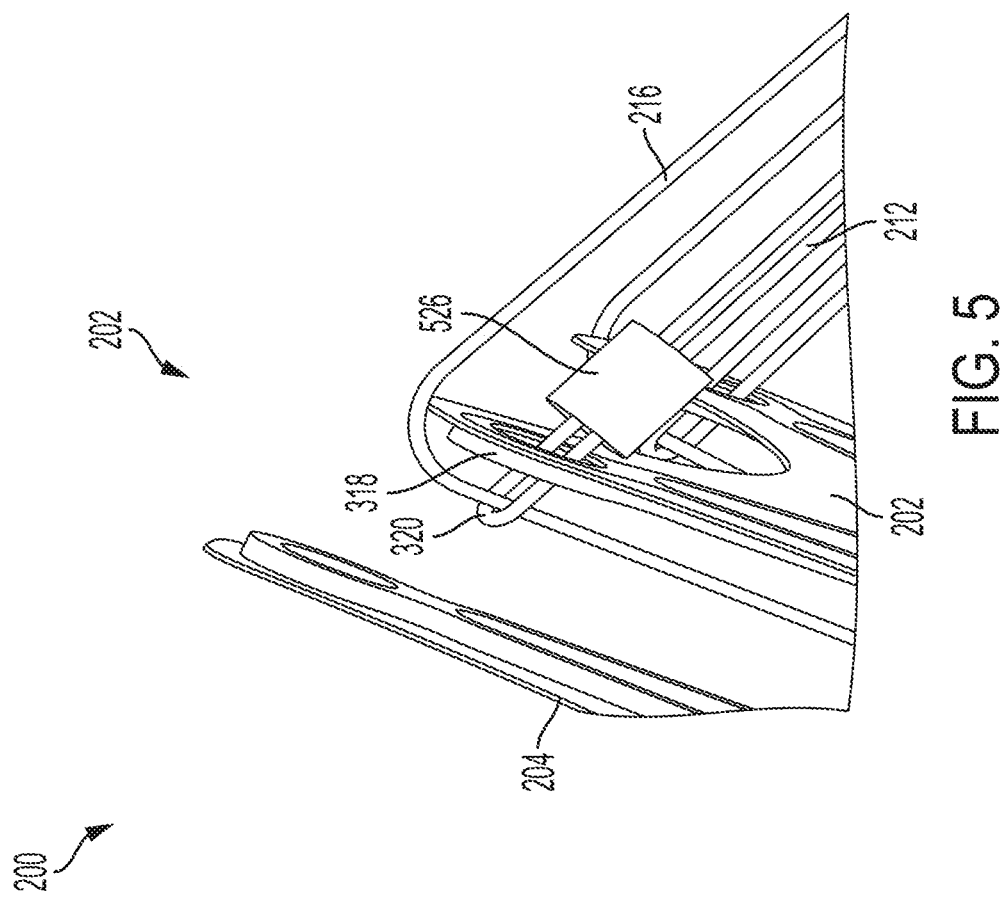
FIG. 5 is another example delivery system including a stop and shunt device in accordance with an embodiment.

FIG. 5 is a delivery system 200 including an example stop 526 and implantable medical device 202 in accordance with an embodiment. The stop 526 is shown arranged at a distal end of a constraining line 212. In certain instances, each of the one or more constraining lines 212 may include the stop 526. The stop 526 is configured to prevent the distal end of the one or more constraining lines 212 from withdrawing from the one or more eyelets 318 of the implantable medical device 202 prior to removal of the one or more release lines 216.

To release or deploy the implantable medical device 202, the one or more release lines 216 are withdrawn to release the one or more constraining lines 212. As shown in FIG. 5, the one or more release lines 216 may be arranged through the constraining loop 320 of the one or more constraining lines 212 and maintain contact between the implantable medical device 202 and the one or more constraining lines 212 during deployment. The one or more release lines 216 are withdrawn to through the constraining loop 320 to facilitate release the one or more constraining lines 212.

Figure 6B:
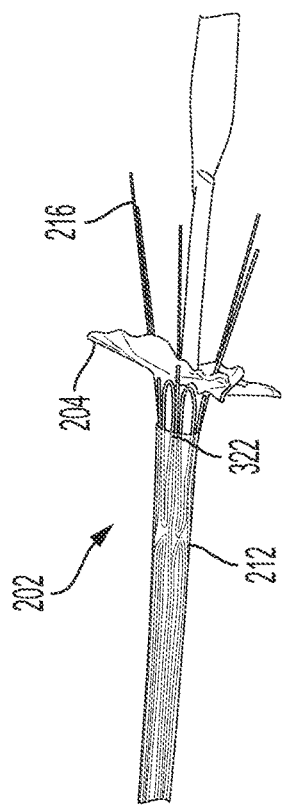
FIGS. 6A-6C show a delivery system in various stages of deploying a shunt device in accordance with an embodiment.
Figure 6C:
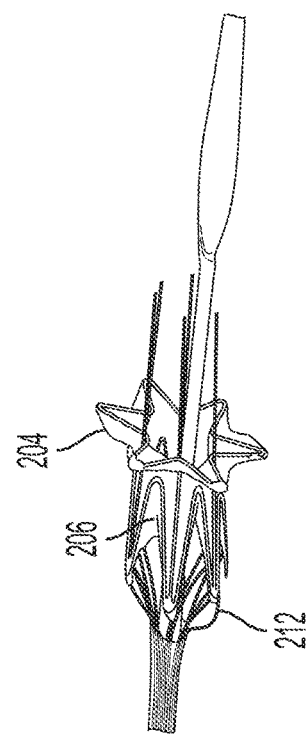
Figure 6A:
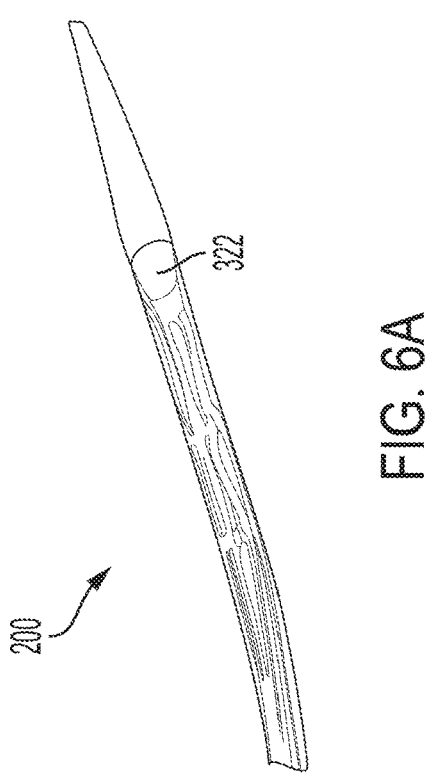

FIGS. 6A-C show a delivery system 200 in various stages of deploying an implantable medical device 202 in accordance with an embodiment. As shown in FIG. 6A, the implantable medical device 202 is shown in a delivery or fully collapsed configuration. As shown, the implantable medical device 202 is arranged within a sheath 322.

The implantable medical device 202 is shown in a partially deployed configuration in FIG. 6B. The implantable medical device 202 may include a first side 204 and a second side 206. The sides 204, 206 are configured to conform to the patient's anatomy (i.e., the first side of the septum, for example). The first side 204 and the second side 206 may be separate and distinct components with a flexible interconnection that connects the two sides in a manner that decouples forces acting on the first side 204 from forces acting on the second side 206. As shown in FIG. 6B, the first side 204 is partially deployed. The sheath 322 has been withdrawn to unconstrain the first side 204 of the implantable medical device 202.

The sheath 322 may be further withdrawn to fully deploy the first side 204 of the implantable medical device 202 as shown in FIG. 6C. The delivery system 200 may also include one or more constraining lines 212 arranged through a portion of the implantable medical device 202. The one or more constraining lines 212 are configured to collapse portions of the implantable medical device 202 (e.g., after the sheath 322 is withdrawn).

As noted above, the delivery system 200 may also include one or more release lines 216 are configured to engage the one or more constraining lines 212 and maintain contact between the implantable medical device 202 and the one or more constraining lines 212 during deployment. The constraining lines 212 and the release lines 216 may facilitate controlled deployment of the second side 206 of the implantable medical device 202. As shown in FIG. 6C, the constraining lines 212 and the release lines 216 may be configured to partially constrain the second side 206 of the implantable medical device 202. The constraining lines 212 and the release lines 216 may be configured to facilitate act as a ramp to guide the implantable medical device 202 from the sheath 322.

Figure 7:
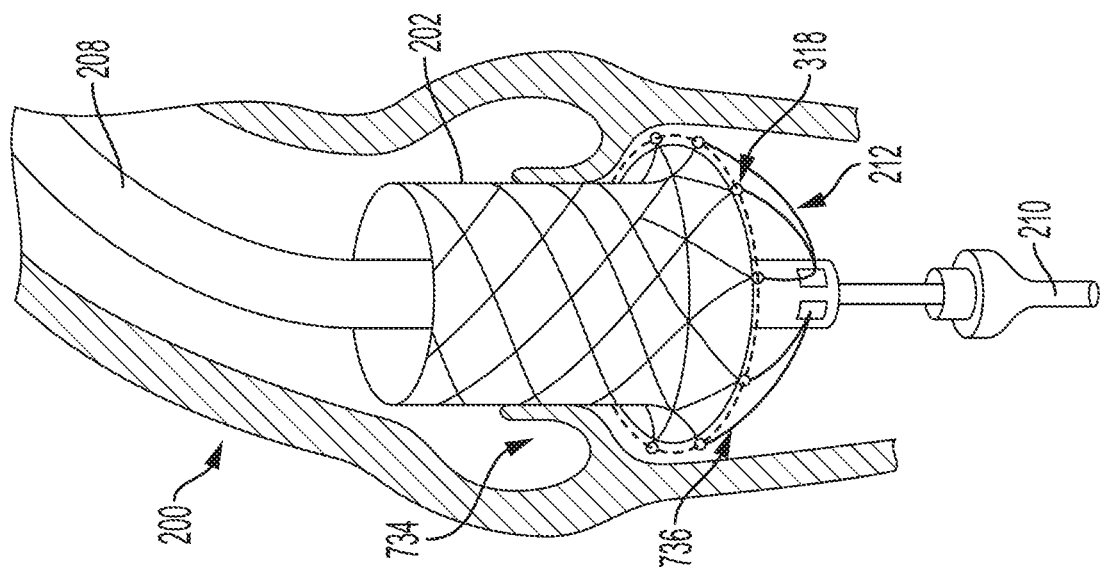
FIG. 7 is another example delivery system and implantable medical device in accordance with an embodiment.

FIG. 7 is another example delivery system 200 and implantable medical device 202 in accordance with an embodiment. The implantable medical device 202 as deployed with the delivery system 200 shown in FIG. 7 may be a replacement heart valve, shunt, stent, stent-graft, valved conduit, or other similar medical device. As shown in FIG. 7, the implantable medical device 202 is a replacement heart valve. As shown, the implantable medical device 202 is implanted across a native valve 734.

The delivery system 200 includes a catheter 208 configured to delivery through a patient's vascular to a delivery site. In certain instances, the delivery system 200 includes a tip 210, that may be atraumatic and may be radiopaque, arranged at a distal end of the catheter 208. The delivery system 200 may also include one or more constraining lines 212 arranged through a portion of the implantable medical device 202. As shown in FIG. 7, the implantable medical device 202 includes eyelets 318 arranged about a circumference of the implantable medical device 202. In certain instances, the implantable medical device 202 includes eyelets 318 arranged at a distal end of the implantable medical device 202 as shown. In other instances, the implantable medical device 202 includes eyelets 318 arranged at a proximal end of the implantable medical device 202. In addition, the implantable medical device 202 may include eyelets 318 arranged at both distal and proximal ends of the implantable medical device 202. In instances where the implantable medical device 202 does not include eyelets 318, the constraining lines 212 and release lines 216 may be arranged through a stent or membrane component of the implantable medical device 202.

The one or more constraining lines 212 may be arranged through the eyelets 318 and configured to collapse portions of the implantable medical device 202 toward the catheter 208. The one or more constraining lines 212 may extend into or attach to the catheter 208 distal of the eyelets 318. The constraining lines 212 may enter into or attach to the catheter 208 proximal to the tip 210. Applying tension to an end (not shown) of the constraining lines 212 collapses the implantable medical device 202 toward the catheter 208 for implantation. As discussed in detail above, the delivery system 200 may include a sheath (not shown) configured to hold the implantable medical device 200 in a collapsed configuration. The constraining lines 212 enable recapture of the implantable medical device 200 after initial deployment. Recapture of the implantable medical device 200 using the constraining lines 212 allows for repositioning of the implantable medical device 200.

In addition, the delivery system 200 may include a secondary constraining element 736 (e.g., a hoop, ring, or other element) that may be arranged about the implantable medical device 202. The one or more constraining lines 212 may be additionally or alternatively (rather than the eyelets 318) arranged with or coupled to the secondary constraining element 736 to facilitate collapsing and expansion of the implantable medical device 202. The delivery systems 200 discussed with reference to FIGS. 2-6 and FIG. 8-FIG. 10 may also utilize the secondary constraining element 736.

Figure 8:
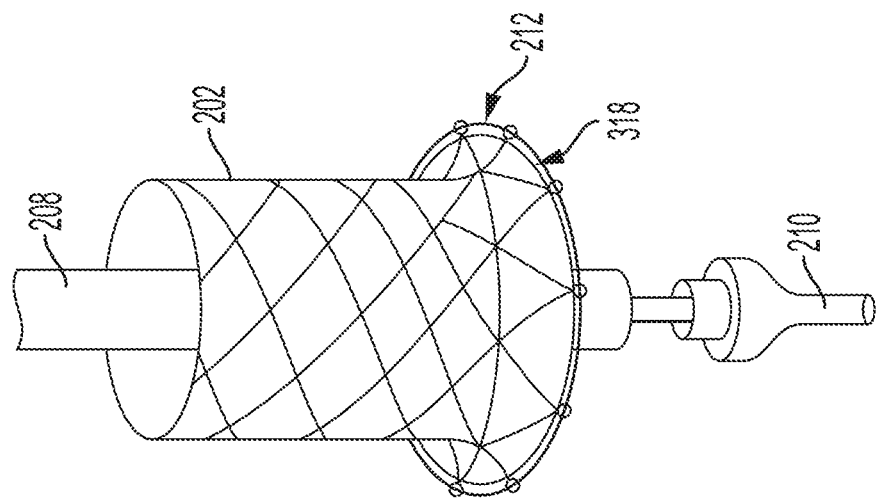
FIG. 8 is another example delivery system and implantable medical device in accordance with an embodiment.

FIG. 8 is another example delivery system 200 and implantable medical device 202 in accordance with an embodiment. The implantable medical device 202 as deployed with the delivery system 200 shown in FIG. 7 may be a replacement heart valve, shunt, stent, stent-graft, valved conduit, or other similar medical device. As shown in FIG. 8, the implantable medical device 202 is a replacement heart valve.

The delivery system 200 includes a catheter 208 configured to delivery through a patient's vascular to a delivery site. In certain instances, the delivery system 200 includes a tip 210, that may be atraumatic and may be radiopaque, arranged at a distal end of the catheter 208. The delivery system 200 may also include one or more constraining lines 212 arranged around a portion of the implantable medical device 202. As shown in FIG. 8, the implantable medical device 202 includes eyelets 318 arranged about a circumference of the implantable medical device 202. In certain instances, the implantable medical device 202 includes eyelets 318 arranged at a distal end of the implantable medical device 202 as shown. In other instances, the implantable medical device 202 includes eyelets 318 arranged at a proximal end of the implantable medical device 202. In addition, the implantable medical device 202 may include eyelets 318 arranged at both distal and proximal ends of the implantable medical device 202. In instances where the implantable medical device 202 does not include eyelets 318, the constraining lines 212 and release lines 216 may be arranged through a stent or membrane component of the implantable medical device 202.

The one or more constraining lines 212 may be arranged through the eyelets 318 and configured to collapse portions of the implantable medical device 202 toward the catheter 208. The one or more constraining lines 212 may be a single line that extends about the implantable medical device 202. Applying tension to an end (not shown) of the constraining lines 212 or line 212 collapses the implantable medical device 202 toward the catheter 208 for implantation. As discussed in detail above, the delivery system 200 may include a sheath (not shown) configured to hold the implantable medical device 200 in a collapsed configuration. The constraining lines 212 enable recapture of the implantable medical device 200 after initial deployment. Recapture of the implantable medical device 200 using the constraining lines 212 allows for repositioning of the implantable medical device 200.

Figure 9B:
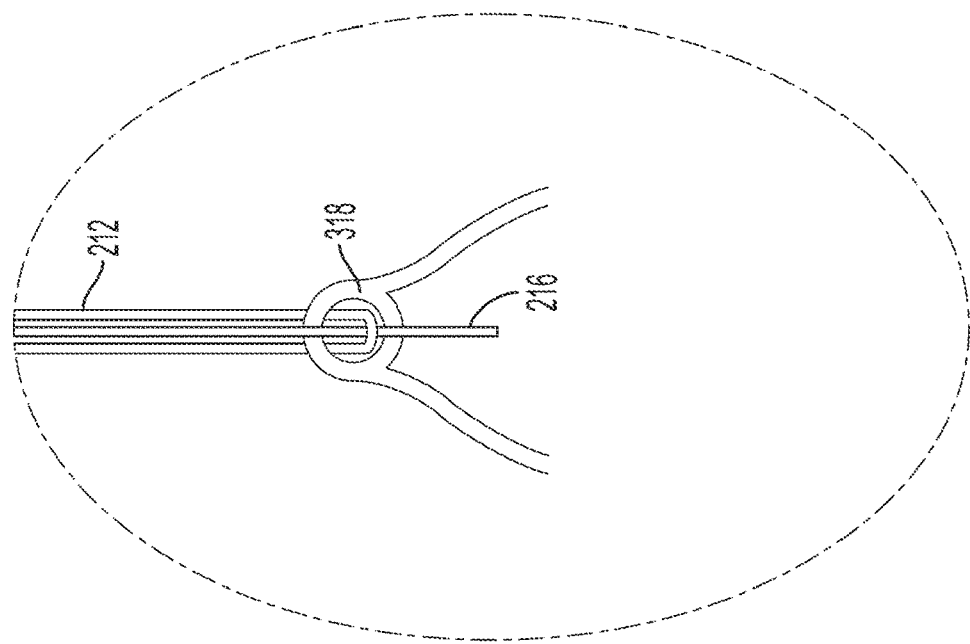
FIG. 9B is a close-up view of a portion of the delivery system shown in FIG. 9A.
Figure 9A:
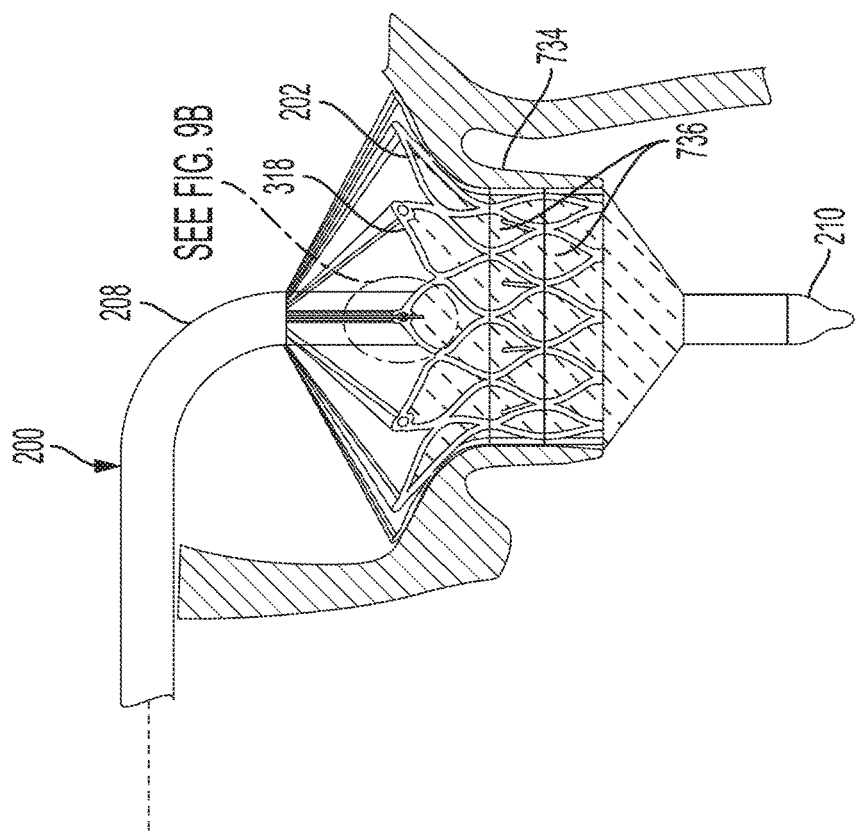
FIG. 9A is another example delivery system and implantable medical device in accordance with an embodiment.

FIG. 9A is another example delivery system 200 and implantable medical device 202 in accordance with an embodiment. The implantable medical device 202 as deployed with the delivery system 200 shown in FIG. 9A may be a replacement heart valve, shunt, stent, stent-graft, or other similar medical device. As shown in FIG. 9A, the implantable medical device 202 is a replacement heart valve. As shown, the implantable medical device 202 is implanted across a native valve 734.

The delivery system 200 includes a catheter 208 configured to delivery through a patient's vascular to a delivery site. In certain instances, the delivery system 200 includes a tip 210, that may be atraumatic and may be radiopaque, arranged at a distal end of the catheter 208. The delivery system 200 may also include one or more constraining lines 212 arranged through a portion of the implantable medical device 202.

As shown in FIG. 9A, the implantable medical device 202 includes eyelets 318 arranged about a circumference of the implantable medical device 202. In certain instances, the implantable medical device 202 includes eyelets 318 arranged at a proximal end of the implantable medical device 202. As shown in further detail with reference to FIG. 9B, the one or more constraining lines 212 may be arranged through the eyelets 318. The one or more constraining lines 212 are configured to collapse portions of the implantable medical device 202 toward the catheter 208. Applying tension to an end (not shown) of the constraining lines 212 collapses the implantable medical device 202 toward the catheter 208 for implantation. As discussed in detail above, the delivery system 200 may include a sheath (not shown) configured to hold the implantable medical device 200 in a collapsed configuration. The constraining lines 212 enable recapture of the implantable medical device 200 after initial deployment. Recapture of the implantable medical device 200 using the constraining lines 212 allows for repositioning of the implantable medical device 200.

The delivery system 200 may also include one or more release lines 216 are configured to engage the one or more constraining lines 212 and maintain contact between the implantable medical device 202 and the one or more constraining lines 212 during deployment. To release or deploy the implantable medical device 202, the one or more release lines 216 are withdrawn to release the one or more constraining lines 212 as discussed in further detail above. The one or more release lines 216 may be arranged through or coupled to the one or more constraining lines 212 and maintain contact between the implantable medical device 202 and the one or more constraining lines 212 during deployment. The one or more release lines 216 are withdrawn to release the one or more constraining lines 212.

Tension applied to the constraining lines 212 to collapse portions of the implantable medical device 202 toward the catheter 208. Tension on an end of the constraining lines 212 not arranged with the implantable medical device 202 retracts the constraining lines 212 into the catheter 208. In certain instances, the sheath (not shown) may also be used to facilitate delivery and constrain the implantable medical device 202. As the constraining lines 212 are retracted into the catheter 208, the implantable medical device 202 may be collapsed into the sheath or catheter 208.

In one example of a deployment sequence, to deploy the implantable medical device 202, the catheter 208 is positioned across the native valve 734, the catheter 208 or a sheath may be retracted to expose a distal portion of the device 202. The catheter 208 may further be retracted to expose the proximal end of the device 202. Prior to release of the constraining lines 212 and the release lines 216, the positioning of the implantable medical device 202 can be evaluated. If the positioning is not satisfactory or desirable, the implantable medical device 202 may be reconstrained and repositioned. To reconstrain and reposition the implantable medical device 202, the constraining sequence described above may be followed (e.g., tension may be applied to the one or more constraining lines 212 and the implantable medical device 202 may be retracted within the sheath or catheter 208). After the implantable medical device 202 is positioned, the constraining lines 212 and the release lines 216 are released.

In certain instances, the delivery system 200 may include a secondary constraining element 736 (e.g., a hoop, ring, or constraining loops as shown) that may be arranged about the implantable medical device 202. The secondary constraining element 736 may be configured to collapse and expand a distal portion of the implantable medical device 202.

Figure 10B:
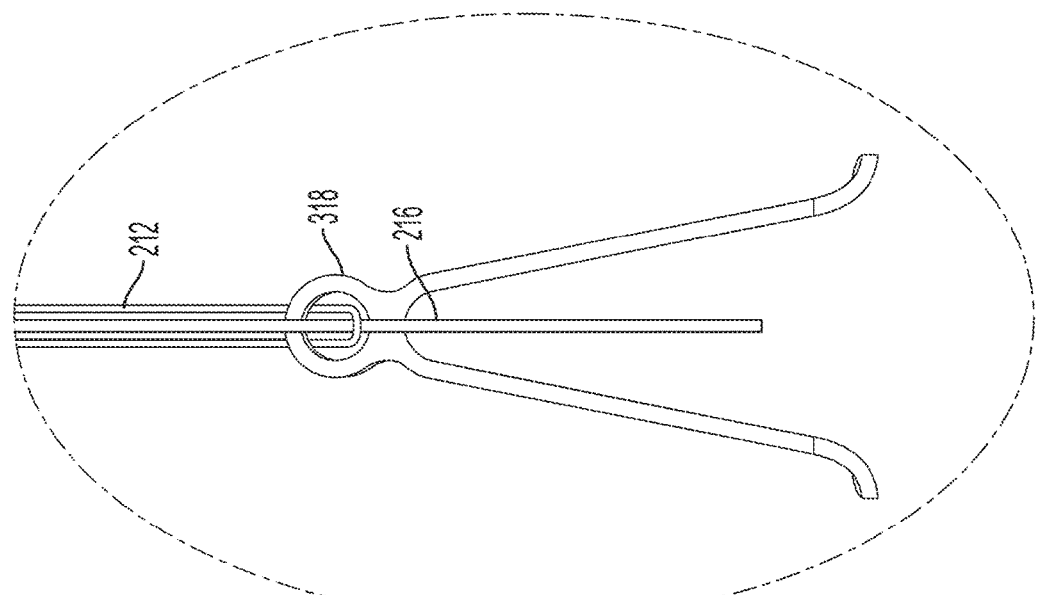
FIG. 10B is a close-up view of a portion of the delivery system shown in FIG. 10A.
Figure 10A:
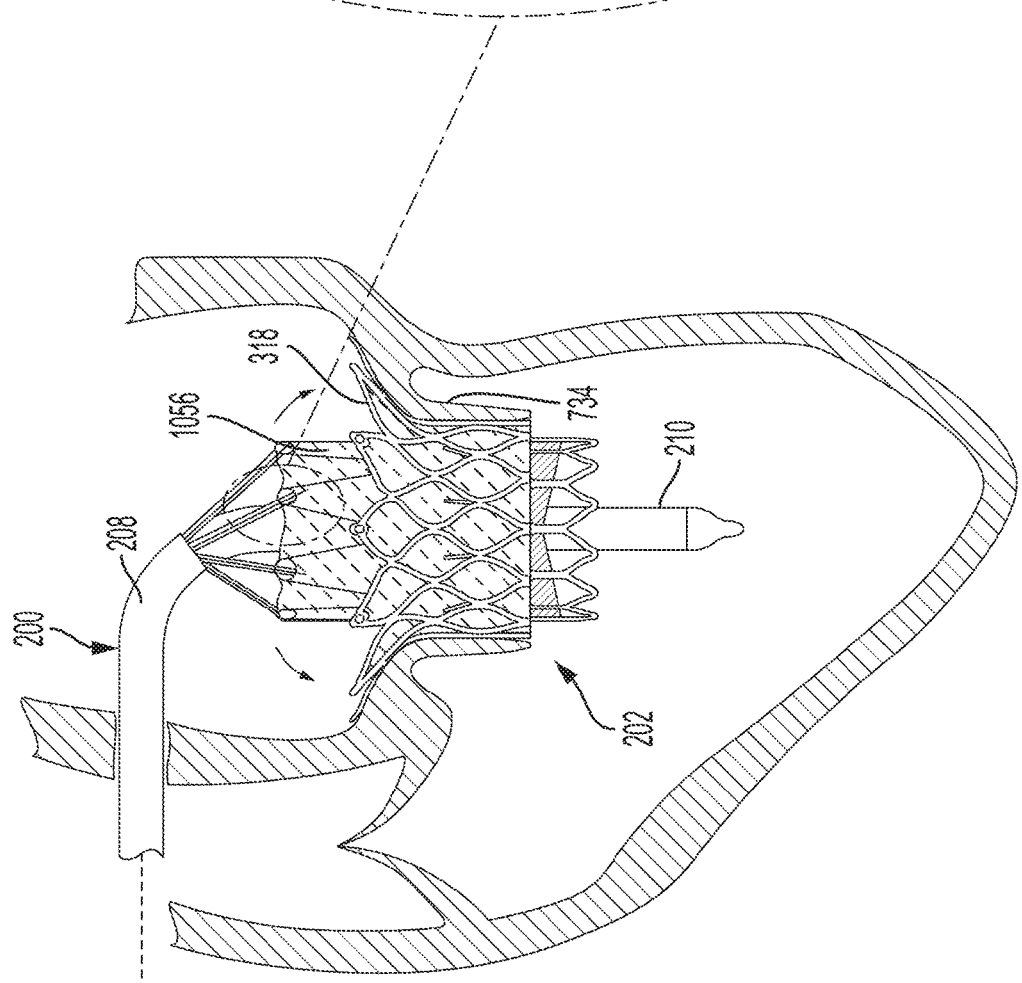
FIG. 10A is another example delivery system and implantable medical device in accordance with an embodiment.

FIG. 10A is another example delivery system 200 and implantable medical device 202 in accordance with an embodiment. The implantable medical device 202 as deployed with the delivery system 200 shown in FIG. 10A may be a replacement heart valve, shunt, stent, stent-graft, or other similar medical device. As shown in FIG. 10A, the implantable medical device 202 is a replacement heart valve. As shown, the implantable medical device 202 is implanted across a native valve 734.

The delivery system 200 includes a catheter 208 configured to delivery through a patient's vascular to a delivery site. In certain instances, the delivery system 200 includes a tip 210, that may be atraumatic and may be radiopaque, arranged at a distal end of the catheter 208. The delivery system 200 may also include one or more constraining lines 212 arranged through a portion of the implantable medical device 202.

As shown in FIG. 10A, the implantable medical device 202 includes eyelets 318 arranged about a circumference of the implantable medical device 202. The eyelets 318 are arranged about a skirt portion 1056 of the implantable medical device 202 that extends from the valve frame structure of the heart valve. In addition and as shown, the constraining liens 212 may be individually arranged through the eyelets 318 and also circumferentially through the eyelets 318 as shown in FIG. 10A.

The delivery system 200 may also include one or more release lines 216 are configured to engage the one or more constraining lines 212 and maintain contact between the implantable medical device 202 and the one or more constraining lines 212 during deployment. To release or deploy the implantable medical device 202, the one or more release lines 216 are withdrawn to release the one or more constraining lines 212 as discussed in further detail above. The one or more release lines 216 may be arranged through or coupled to the one or more constraining lines 212 and maintain contact between the implantable medical device 202 and the one or more constraining lines 212 during deployment. The one or more release lines 216 are withdrawn to release the one or more constraining lines 212.

Tension applied to the constraining lines 212 to collapse portions of the implantable medical device 202 toward the catheter 208. Tension on an end of the constraining lines 212 not arranged with the implantable medical device 202 retracts the constraining lines 212 into the catheter 208. In certain instances, the sheath (not shown) may also be used to facilitate delivery and constrain the implantable medical device 202. As the constraining lines 212 are retracted into the catheter 208, the implantable medical device 202 may be collapsed into the sheath or catheter 208.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A deployment system for an implantable medical device, the system comprising:
   an implantable medical device including a first side, a second side, and a conduit portion extending therebetween, wherein at least one of the first side and the second side extends away from the conduit portion relative to a longitudinal axis and at least one of the first or second sides including lobes defining one or more eyelets;
   a catheter having a first end and a second end;
   a tip coupled to the first end of the catheter
   one or more constraining lines arranged through the one or more eyelets of the implantable medical device, the one or more constraining lines being configured to collapse portions of the implantable medical device toward the catheter; and
   one or more release lines configured to engage the one or more constraining lines and maintain contact between the implantable medical device and the one or more constraining lines during deployment, the one or more release lines being at least partially nested in the tip;
   wherein the one or more release lines are configured to withdraw to release the one or more constraining lines,
   wherein the one or more constraining lines include a constraining loop at a distal end of the one or more constraining lines, and the one or more release lines are arranged through the constraining loop of the one or more constraining lines to maintain contact between the implantable medical device and the one or more constraining lines during deployment,
wherein the implantable medical device further comprises a membrane and a frame, and wherein the constraining loop of the one or more constraining lines is positioned through the one or more eyelets such that the one or more release lines is positioned only exterior to the frame.

2. The system of claim 1, wherein the one or more constraining lines are configured to engage the one or more eyelets on at least the first side of the implantable medical device.

3. The system of claim 1, further comprising a sheath arranged about the catheter and configured to capture the collapsed implantable medical device.

4. The system of claim 3, wherein the sheath is configured to constrain the implantable medical device.

5. The system of claim 1, wherein the one or more constraining lines are one or more constraining wires.

6. The system of claim 1, further comprising a stop arranged on the catheter and configured to limit movement of the implantable medical device in a direction opposite that of a direction in which tension is applied to the one or more constraining lines.

7. The system of claim 1, further comprising one or more stops arranged distal to the distal end of the one or more constraining lines and configured to prevent the distal end of the one or more constraining lines from withdrawing from the one or more eyelets of the implantable medical device prior to removal of the one or more release lines.

8. The system of claim 1, wherein the one or more release lines are configured to facilitate deployment and act as a ramp to guide the implantable medical device from a sheath.

9. The system of claim 1, wherein the implantable medical device is one of a shunt device, a heart valve, or a valved conduit.

10. The system of claim 1, wherein the one or more constraining lines are engaged only with the one or more eyelets on one of the first side or the second side of the implantable medical device.

11. The system of claim 1, wherein the one or more release lines are configured to radially pull down the first side of the implantable medical device.

12. The system of claim 1, wherein the implantable medical device is a shunt.

13. The system of claim 1, wherein the first side and the second side of the implantable medical device are separate and distinct components such that the conduit portion is a flexible interconnection that coupled the first side and the second side such that the flexible interconnection is operable to decouple forces acting on the first side from forces acting on the second side.

14. The system of claim 1, wherein the first side and the second side of the implantable medical device are configured to be angulated toward the longitudinal axis during delivery.

15. A deployment system comprising:
an implantable medical device including a first side, a second side, and a conduit portion extending therebetween, wherein the first side and the second side of the implantable medical device are configured to be angulated toward the longitudinal axis during delivery;
a catheter having a first end and a second end;
a tip coupled to the first end of the catheter;
a sheath configured to hold the implantable medical device in a collapsed configuration;
one or more constraining lines arranged through a portion of the implantable medical device and configured to collapse portions of the implantable medical device toward the catheter in response to tension applied to the one or more constraining lines and allow expansion of the implantable medical device in response to release of the tension, wherein the one or more constraining lines are engaged only with eyelets of the implantable medical device on one of the first side or second side of the implantable medical device; and
one or more release lines configured to engage the one or more constraining lines and maintain contact between the implantable medical device and the one or more constraining lines during deployment and withdraw to release the one or more constraining lines to deploy the implantable medical device to a deployed configuration, wherein the one or more release lines are at least partially nested in the tip;
wherein the one or more constraining lines include a constraining loop at a distal end of the one or more constraining lines, and the one or more release lines are arranged through the constraining loop of the one or more constraining lines to maintain contact between the implantable medical device and the one or more constraining lines during deployment,
wherein the implantable medical device further comprises a membrane and a frame, and wherein the constraining loop of the one or more constraining lines is positioned through the eyelets such that the one or more release lines is positioned only exterior to the frame.

16. The deployment system of claim 15, wherein the eyelets are arranged about a circumference of the implantable medical device and the one or more constraining lines are arranged through the eyelets.

17. The deployment system of claim 15, wherein at least one of the one or more constraining lines and the one or more release lines are coupled to the catheter near the first end thereof.

18. The deployment system of claim 17, wherein at least one of the one or more constraining lines and the one or more release lines are coupled to the catheter adjacent the tip.

19. A method of deploying an implantable medical device, the method comprising:
arranging a catheter at a target location with the implantable medical device arranged within a collapsed configuration within a sheath, wherein the implantable device includes a first side and a second side that are separate and distinct components and a conduit portion that is a flexible interconnection that couples the first side and the second side such that the flexible interconnection is operable to decouple forces acting on the first side from forces acting on the second side;
allowing expansion of at least a portion of the implantable medical device by releasing tension on one or more constraining lines arranged through one or more eyelets of the implantable medical device, wherein one or more release lines are at least partially nested in a tip coupled to a first end of the catheter; and
wherein the one or more constraining lines include a constraining loop at a distal end of the one or more constraining lines, and the one or more release lines are arranged through the constraining loop of the one or more constraining lines to maintain contact between the implantable medical device and the one or more constraining lines during deployment;

releasing the one or more constraining lines from the implantable medical device by removing the one or more release lines engaged with the one or more constraining lines, wherein the one or more release lines are configured to withdraw to release the one or more constraining lines, wherein the implantable medical device further comprises a membrane and a frame, and wherein the constraining loop of the one or more constraining lines is positioned through the one or more eyelets such that the one or more release lines is positioned only exterior to the frame.

20. The method of claim 19, further comprising advancing the sheath to deploy the first side of the implantable medical device and wherein allowing expansion of the portion of the implantable medical device includes allowing expansion of the second side of the implantable medical device by releasing tension on the one or more constraining lines.

21. The method of claim 20, further comprising reconstraining the implantable medical device by applying tension to the one or more constraining lines and retracting the implantable medical device within the sheath.

22. The method of claim 20, further comprising deploying the second side of the implantable medical device by releasing tension applied to the one or more constraining lines.

* * * * *